(12) United States Patent
Demir

(10) Patent No.: US 11,039,937 B2
(45) Date of Patent: Jun. 22, 2021

(54) EXPANSION APPARATUS

(71) Applicant: TOBB EKONOMI VE TEKNOLOJI UNIVERSITESI, Ankara (TR)

(72) Inventor: Teyfik Demir, Ankara (TR)

( * ) Notice: Subject to any disclaimer, the term of this patent is extended or adjusted under 35 U.S.C. 154(b) by 157 days.

(21) Appl. No.: 16/472,989

(22) PCT Filed: Dec. 28, 2017

(86) PCT No.: PCT/TR2017/050714
§ 371 (c)(1),
(2) Date: Jun. 24, 2019

(87) PCT Pub. No.: WO2018/208269
PCT Pub. Date: Nov. 15, 2018

(65) Prior Publication Data
US 2019/0328547 A1      Oct. 31, 2019

(30) Foreign Application Priority Data

Dec. 30, 2016   (TR) .................. 2016/20379

(51) Int. Cl.
*A61F 2/46*       (2006.01)
(52) U.S. Cl.
CPC ..... *A61F 2/4611* (2013.01); *A61F 2002/4615* (2013.01); *A61F 2002/4627* (2013.01)
(58) Field of Classification Search
CPC ........... A61B 17/70; A61F 2002/30538; A61F 2002/30593; A61F 2002/30235; A61F 2002/30487; A61F 2002/30556; A61F 2002/30601; A61F 2002/304; A61F 2002/30904; A61F 2002/4615; A61F 2002/4627; A61F 2002/30579; A61F 2002/3052; A61F 2002/30136
See application file for complete search history.

(56) References Cited

U.S. PATENT DOCUMENTS

| 2013/0274883 A1* | 10/2013 | McLuen ................... A61F 2/28 623/17.16 |
| 2014/0094917 A1 | 4/2014 | Salerni |
| 2016/0338846 A1* | 11/2016 | Walker ................. A61F 2/4611 |
| 2018/0036137 A1* | 2/2018 | Levieux ............... A61F 2/4455 |

FOREIGN PATENT DOCUMENTS

WO       2016142282 A1     9/2016

OTHER PUBLICATIONS

International Search Report for corresponding PCT/TR2017/050714.

* cited by examiner

*Primary Examiner* — Pedro Philogene

(57) ABSTRACT

An expansion apparatus is used in spinal surgery, and which opens the expandable cage located between the vertebrae during the operation in a preferred amount, and thus adjusts the distance between the vertebrae as desired.

4 Claims, 3 Drawing Sheets

EXPANSION APPARATUS

FIELD OF THE INVENTION

Figure 1:
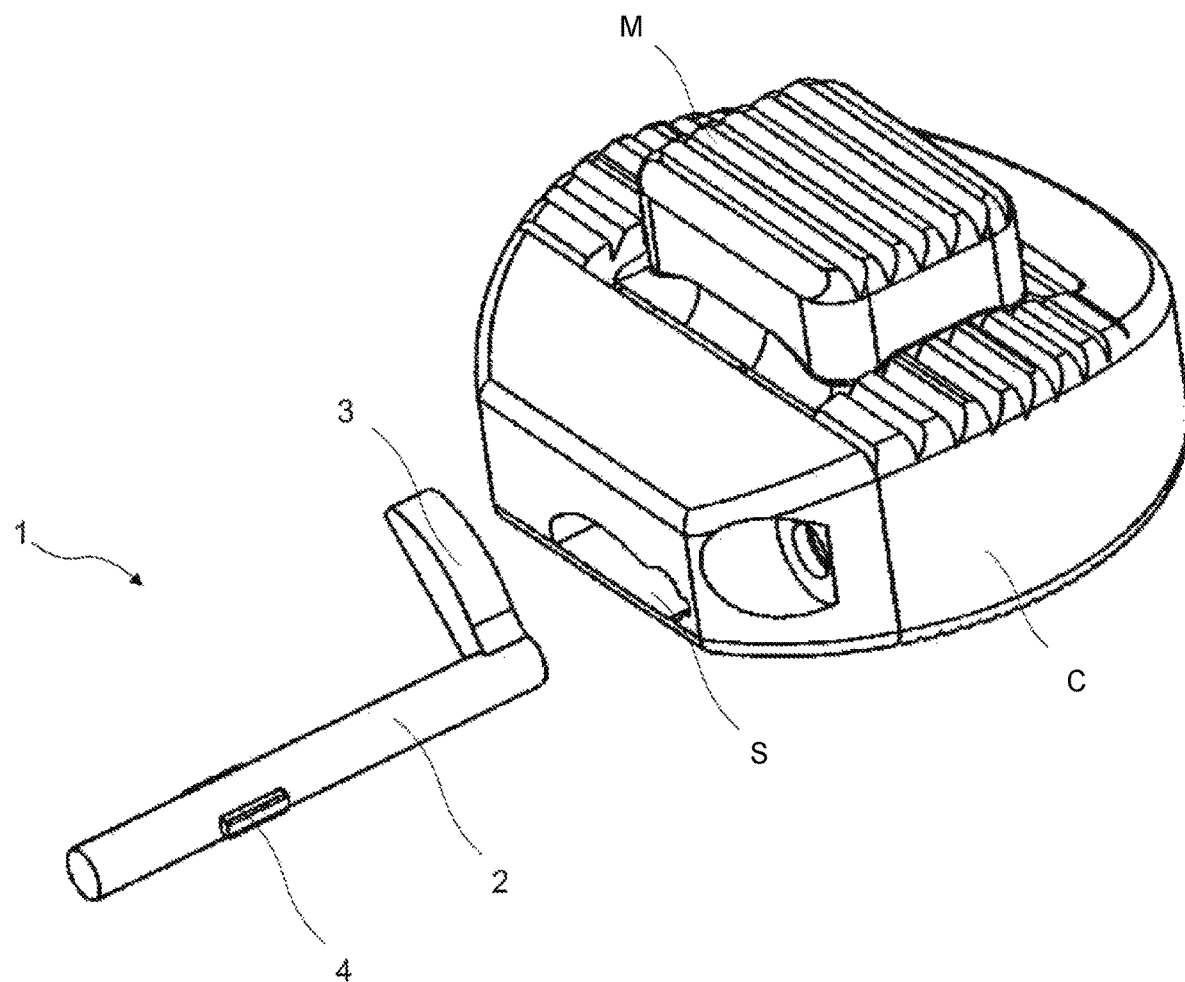

The present invention relates to an expansion apparatus which is used in spinal surgery, opens the expandable cage located between the vertebrae during the operation in a preferred amount, and thus adjusts the distance between the vertebrae as desired.

BACKGROUND OF THE INVENTION

Herniated disc and cervical disc hernia result from displacement of the disc between the vertebrae towards the ependymal canal, and thus applying pressure on the nerves and on the spinal cord.

It is typically sufficient, for the diagnosis and identifying the location of the disk herniation, to carefully examine any loss of strength, loss of sense or abnormal reflex in addition to a clinical evaluation for determining the type and location of the pain. As a result of herniation, acute pain and loss of sense may occur in the area of the hernia. It is only possible with surgical intervention to eliminate such pain and loss of sense in some patients. In parallel with the advances in technology, cervical disc hernia surgery can be performed in smaller spaces than before. The patients are operated through anterior or posterior cervical spine. In case of operations through the anterior cervical spine, the region between two vertebrae is emptied and the disc between said vertebrae is removed, and subsequent to cleaning this region, a cage, into which bone graft is added and which prevents collapse between the vertebrae, is located.

The cage configurations used in the state of the art are typically sized by taking the distance between the vertebrae of the patient as an average. However, the provision of cage configurations with adjustable height is crucial since the anatomy and vertebral column length differ from one patient to another. Such cage configurations can be made of various materials, particularly of metal, carbon, and polyetheretherketone (PEEK).

In the state of the art, the cages adjustable according to the distance between the vertebrae are utilized for being located between the vertebrae. Thanks to such cage configurations, an expandable cage can be adjusted in accordance with the height of the patient. In other words, it is no longer necessary to manufacture cages with different sizes for each patient.

In the art, there exist no expansion apparatus which allows the adjustment of the cages, which are located between two vertebrae and maintain the distance between two vertebrae in the preferred manner, in vertical axis, and thus opens the distance between two vertebrae in a preferred amount, and which generally has a "cam" geometry (L-shaped dagger-like geometry).

OBJECTS OF THE INVENTION

The object of the present invention is to provide an expansion apparatus which facilitates positioning of the cage, which will be located between two vertebrae, by the operator.

Another object of the present invention is to provide an expansion apparatus which enables the expandable cage, which is located between two vertebrae, to form the preferred intervertebral distance.

And another object of the present invention is to provide an expansion apparatus which allows easy access to the expandable cage, which is located between the vertebrae.

BRIEF DESCRIPTION OF THE INVENTION

An expansion apparatus which has been developed for achieving the objects of the invention and is defined in the first claim and other dependent claims comprises a body and a moving edge disposed at one end of the body. The body is provided thereon with two protrusions. The operator places the expansion apparatus in the space of the cage located between the vertebrae and applies a rotational force on the body such that the expandable cage will expand between the vertebrae in a preferred amount. The body rotates upon the applied force. With the rotation of the body, the moving edge disposed in the cage contacts with an extension comprised by the cage and makes the movable part of the cage move in vertical axis, thereby allowing the expandable cage to open, i.e. expand, in a preferred amount.

DETAILED DESCRIPTION OF THE INVENTION

The expansion apparatus developed for achieving the objects of the present invention is illustrated in the accompanying drawings, in which;

FIG. 1. Perspective view of the expansion apparatus from an angle.

Figure 2:
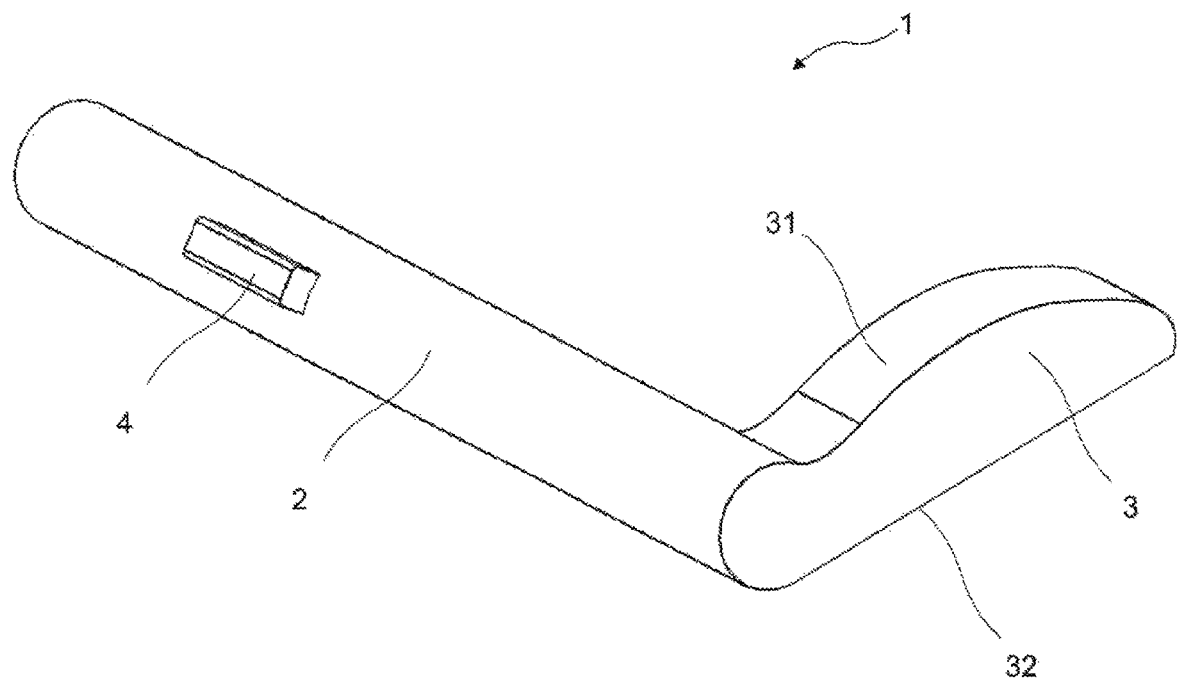

FIG. 2. Perspective view of the expansion apparatus from another angle.

Figure 3:
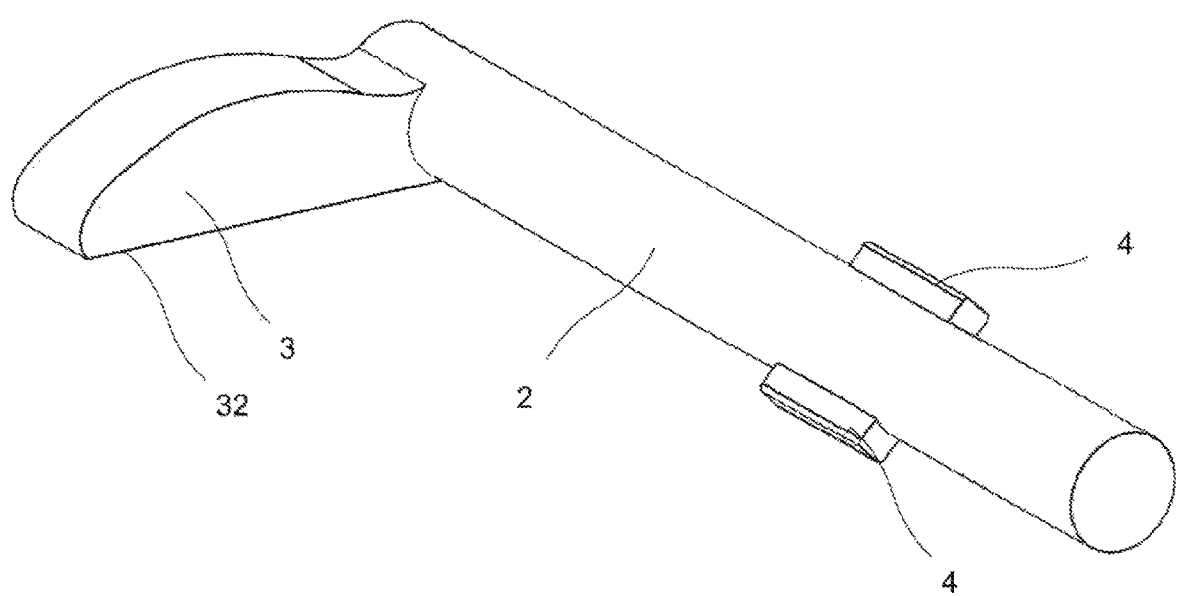

FIG. 3. Perspective view of the expansion apparatus from another angle.

Figure 4:
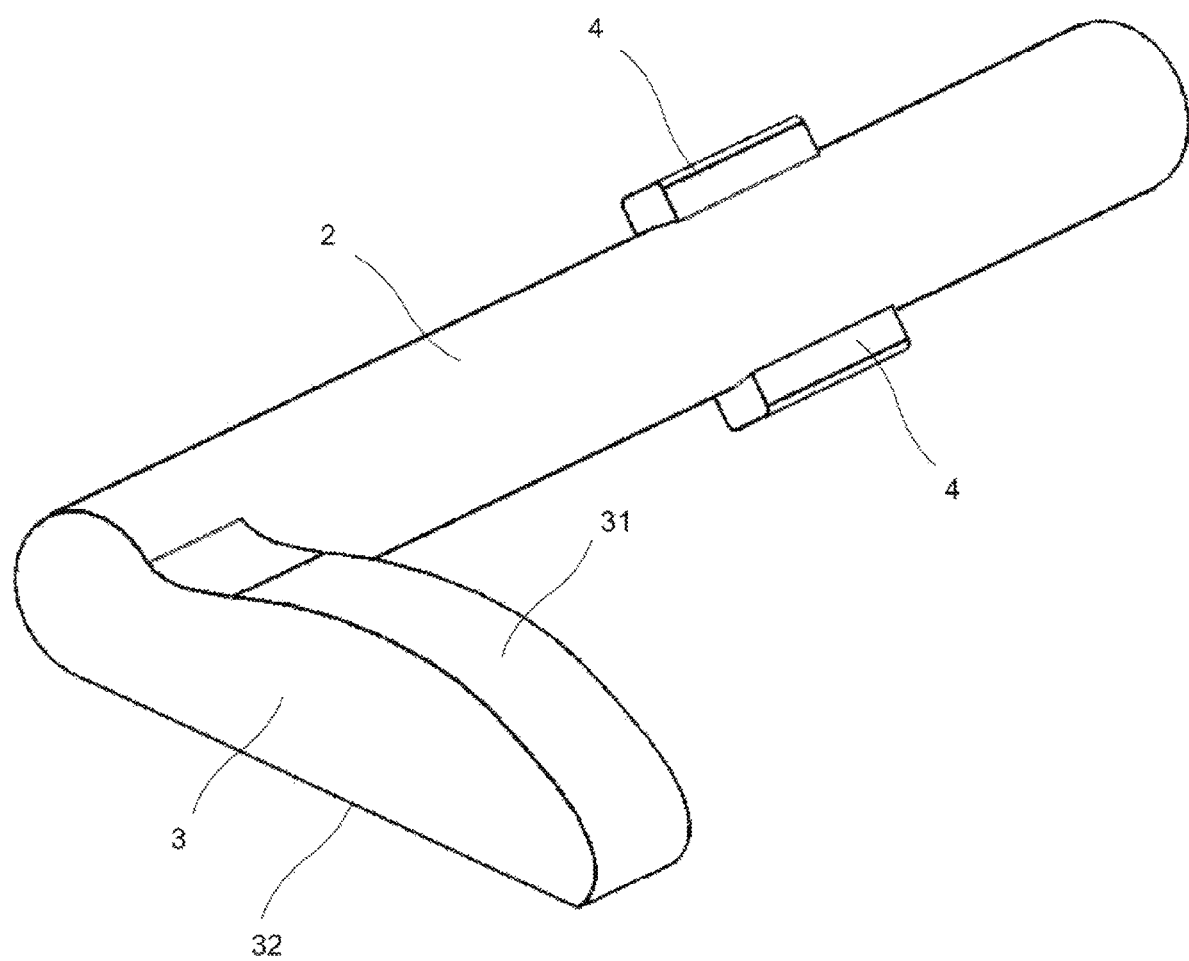

FIG. 4. Perspective view of the expansion apparatus from another angle.

The components in the drawings are enumerated individually and the reference numbers corresponding thereto are given below.

1. Expansion apparatus
2. Body
3. Moving edge
   31. Upper surface
   32. Lower surface
4. Protrusion
C. Cage
S. Space
M. Movable part An expansion apparatus (1) which is used in spinal surgery, opens the expandable cage (C) located between the vertebrae during the operation in a preferred amount in vertical axis, and thus adjusts the distance between the vertebrae as desired, basically comprises:

- at least one body (2) which the operator contacts with and applies a force on,
- at least one moving edge (3) which is placed in the space (S) disposed on the cage (C) and performs, upon a rotational force acting on the body (2), a rotational movement, and thus makes the movable part (M) of the cage (C) move in vertical axis, said moving edge typically having a "cam" geometry, and
- at least one protrusion (4) which is disposed on the body (2) and permits a holding means, which enables the operator to apply a force on the body (2), to be secured on the body (2).

In an embodiment of the invention, there exists a body (2). The body (2) presents the main structure of the expansion apparatus (1). The body (2) may have the preferred geometry. In this embodiment, the body (2) has a cylindrical form. The operator applies a rotational force on the body (2) during the operation. The body (2) rotates upon the applied force and makes the moving edge (3) rotate together with it.

In an embodiment of the invention, there exists a moving edge (3). The moving edge (3) contacts with an extension comprised by the cage (C) and transfers the force applied thereon during the movement to the extension, and thus making the movable part (M) move in the preferred direction. The moving edge (3) is provided at one end of the body (2) and typically has a "cam" geometry. The moving edge (3) may be integrated with the body (2), or a separate part to be mounted in the body (2). In this embodiment of the invention, the moving edge (3) is integrated with the body (2). The moving edge (3) may have the desired geometry. In this embodiment of the invention, the moving edge (3) comprises an upper surface (31) and a lower surface (32). The upper surface (31) preferably has a sinusoidal form and contacts with an extension comprised by the cage (C). While the moving edge (3) is making the movable part (M) move in vertical axis, the upper surface (31) is in contact with the extension of the movable part (M) and transfers the rotational force applied by the operator to the extension. The lower surface (32) preferably has a planar configuration.

In an embodiment of the invention, there exists a protrusion (4) on the body (2). The protrusion (4) enables the operator to secure a holding means on the expansion apparatus (1). With a holding means being secured in the protrusions (4) disposed on the body (2), the operator can apply a force on the body (2) by means of the holding means. There may be as many protrusions (4) on the body (2) as desired. In this embodiment of the invention, two protrusions (4), preferably with a rectangular geometry, are provided on the body (2) such that they are located in parallel to one another.

The expansion apparatus (1) in this embodiment of the invention is used as follows. After the damaged intervertebral disc is removed, the region of the disc is cleaned. Subsequent to cleaning, the cage (C) is located between the vertebrae. Afterwards, the expansion apparatus (1) is located in the space (S) provided on the cage (C) according to the distance between the vertebrae. In such position, the expansion apparatus (1) is in contact with an extension provided in the lower surface of the movable part (M). The expansion apparatus (1) is rotated clockwise or counterclockwise at a certain angle. With the rotation of the expansion apparatus (1), the extension with which it is in contact, and hence the movable part (M) can be brought to the preferred height. Once the movable part (M) is brought to the preferred height, it is fixed. After the preferred intervertebral distance is adjusted, the expansion apparatus (1) is removed from the space (S) and the positioning of the expandable cage (C) between the vertebrae is thus completed.

The invention claimed is:

1. An expansion apparatus for use in spinal surgery, the expansion apparatus comprising:
    an expandable cage having a movable part therein, the expandable cage adapted to be positioned between a pair of vertebrae, the movable part being movable along a vertical axis and adapted to bear against one of the pair of vertebrae so as to adjust a distance between the pair of vertebrae, said expandable cage having a space beneath or above the movable part;
    a body having a cam affixed or integrated thereto, said body being removably received in said expandable cage such that the cam resides in the space beneath or above the movable part, said body having a portion away from the cam extending outwardly of said expandable cage, said body being rotatable such that the cam bears against the movable part so as cause the movable part to move along the vertical axis; and
    at least one protrusion disposed on said body outwardly of said expandable cage, said at least one protrusion extending radially outwardly of said body, said at least one protrusion adapted to enable an operator to apply a rotational force thereto such that said body and the cam rotate.

2. The expansion apparatus of claim 1, wherein said body has a cylindrical configuration.

3. The expansion apparatus of claim 1, wherein the cam has an upper surface contacting the movable part, the upper surface having a sinusoidal form.

4. The expansion apparatus of claim 1, wherein said at least one protrusion comprises a pair of protrusions diametrically opposed to each other on said body.

* * * * *